United States Patent [19]

Tabor, Jr. et al.

[11] Patent Number: 4,915,225

[45] Date of Patent: Apr. 10, 1990

[54] SAFETY NEEDLE CAP HANDLER

[76] Inventors: William D. Tabor, Jr., 205 Danville Ave.; James V. Blackwell, 19503 Foxbrook Dr., both of Colonial Heights, Va. 23834

[21] Appl. No.: 192,180

[22] Filed: May 9, 1988

[51] Int. Cl.[4] .............................................. B65D 83/10
[52] U.S. Cl. .................................... 206/368; 206/438; 206/364
[58] Field of Search ............... 206/365, 367, 368, 438; 604/110, 192; 81/3.08

[56] References Cited

U.S. PATENT DOCUMENTS 4,615,242 10/1986 Milin ..................................... 81/3.08
4,742,910 5/1988 Staebler ............................... 206/365

Primary Examiner—Allen M. Ostrager

[57] ABSTRACT

A device to be mounted to a wall, cabinet, counter, or other surface in the dental operatory or medical facility that will securely hold the protective needle cap provided on disposable needles used on dental syringes, or other syringes of similar design, in order that the needle cap may be removed and replaced without risk of an infectious needle stick injury. This is accomplished by engaging a raised annular ridge on the outer surface of the needle cap against an internal shoulder at the open end of a specially shaped trough, sized to accommodate the needle cap. A spring at the other end of the trough provides a rearward force to keep the annular ridge of the needle cap firmly engaged against the internal shoulder at the open end of the trough.

1 Claim, 1 Drawing Sheet

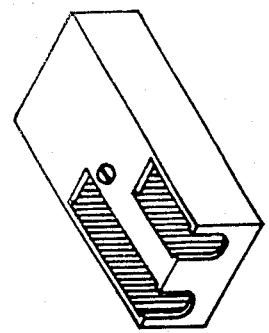
Fig. 3
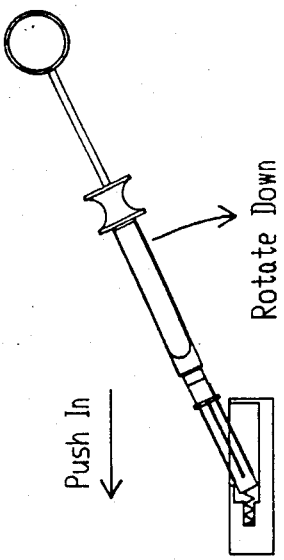
Fig. 4
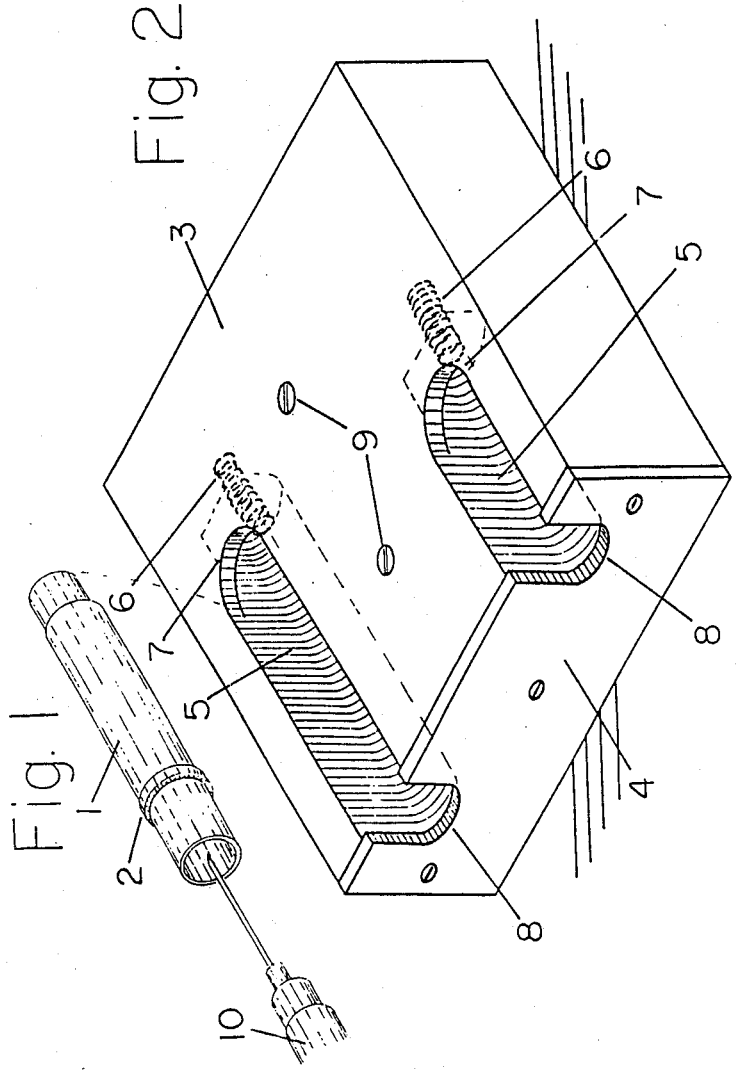
Fig. 1
Fig. 2

SAFETY NEEDLE CAP HANDLER

FIELD OF INVENTION:

This invention is a safety device intended to reduce the risk of exposure of health care personnel to blood borne diseases (including AIDS and Hepatitis B) due to accidental needle stick injury incurred while handling and recapping non-disposable hypodermic syringes, particularly of the type used in dental offices.

DISCUSSION OF PRIOR ART:

The syringes used to administer local anesthetics in dental offices and other similar syringes use a disposable carpule (cartridge) of local anesthetic and a disposable needle which attaches to the front of the syringe. The disposable needle is supplied by the manufacturer with a two part protective cover. The back part of the cover fits over the mounting hub of the needle and 1 centimeter of the back end of the front cover and is removed and discarded when the syringe is loaded for use. The front portion remains as a protective cover to preserve the sterility of the needle and to protect the users while handling the syringe prior to use. The front portion of the protective cover is referred to as a "needle cap". (FIG. 1-1) Because of the manner in which the back portion of the cover telescopes over the front portion and the two are sealed together, an annular ridge (2) or shoulder is created 1 centimeter from the back end of the front portion of the cap. All commercially available needles for dental office use at this time have a similar ridge or shoulder. The needles and their protective needle caps intended for use in dental offices are supplied in different lengths for use in Mandibular and Maxillary injections. The Mandibular needle cap is 4.5 to 5 centimeters long from the previously mentioned shoulder to the front end and the Maxillary needle cap is 3 to 3.5 centimeters long between those points. The diameter of the cap at the shoulder is 1 centimeter and immediately behind the shoulder the diameter is less, usually 0.85 centimeters.

The needle cap is removed immediately prior to administering the injection to the patient. The danger of an infectious needle stick occurs when the protective needle cap is replaced on the needle which is now contaminated with the patient's blood and saliva after the injection is completed. The syringe is held in the operator's favored hand and the needle cap is held in the other. If the needle (10) misses the opening in the cap, the hand holding the cap will be stuck and the operator exposed to any blood-borne infection carried by the patient. To avoid this problem, the Center for Disease Control currently recommends discarding disposable syringes without replacing the needle cap. This is impractical in the dental office because only the needle, its covers, and the anesthetic carpule (or cartridge) are disposable, the remainder of the syringe is sterilized and reloaded. The risk of an accidental stick is greater handling the uncapped syringe needle than the risk to recap the needle. There are techniques for handling the recapping procedure to avoid the danger of of a stick such as "scooping" the cap off a table top with the needle and pressing the cap against a wall to seat the cap on the needle base or holding the cap with a hemostat or forcep instead of the hand. These techniques work, but they are awkward at best and often ignored out of convenience.

The problem of needle sticks has been addressed by inventors in several ways. Revelant prior patents were found in class 604, subclasses 110 and 192. The approaches fall into three general categories: modifications of the syringe or needle cap, shields to protect the holding hand (either integral to the needle cap or attached), and holders for the needle cap allowing the hands to remain out of the area of danger.

The first approach requires the use of a disposable syringe in which the needle is withdrawn into the body of the syringe or part of the syringe or needle cap slides down over the needle after the syringe has been used. These are single use syringes and disposable themselves after one injection making them impractical for use in the dental office. An example of this approach is Patent No. 4,026,287 granted to Irene Haller on May 31, 1977. (Copy enclosed)

The second approach involves shielding the hand holding the needle cap with an extension of the rim of the needle cap. These devices require the use of two hands for the uncapping and re-capping procedure and are somewhat inconvenient. An example of this approach is Patent No. 4,623,336 granted to James J. Pedicano on Nov. 18, 1986. (Copy enclosed)

The third approach is to use a device, either hand held or mounted to a stationary object, to hold the needle cap while the needle is reinserted into the cap, thereby keeping the hand out of the area of danger. Patent No. 4,596,562 granted to Jonathon T. Vernon on June 24, 1986 (copy enclosed) is an example of a hand held device of this type. Patent No. 4,717,386 granted to John Simmons on Jan. 5, 1988 (copy enclosed) includes embodiments of both hand held and stationary mounted types.

In previous inventions of this type, including those mentioned above, the needle cap is retained by friction, usually obtained by forcing a tapered needle cap of the type found on disposable syringes into a hole larger than the small end of the needle cap but smaller than the large end. One-handed operation of a device of this type when removing the needle cap depends on generating a frictional retaining force between the outer surface of the needle cap and the inner surface of the device that is greater than the frictional retaining force holding the cap on the needle hub. This is unreliable. If onehanded removal of the needle cap is accomplished, it then becomes necessary to grasp the needle cap directly after the needle has been replaced in the cap in order to remove the syringe, needle, and its protective cap from the device. Although such a maneuver is safe, it is somewhat awkward. Since the needle caps used on dental syringes have parallel sides rather than tapered, one-handed operation of this type of device is impossible.

I am an actively practicing dentist and would probably be aware of any products of this type that may be on the market for use in dental offices. I am aware of only one device currently being promoted for recappng dental syringe needles, the Jenker AntiNeedlestick Device which is imported from England by the Ash division of Dentsply in York, Pennsylvania. It is my understanding that a US patent is pending on this device. It is a simple, truncated metal cone approximately 4 CM tall by 4 CM wide at the base, with a hole approximately 1.2 CM in diameter bored 3 CM deep from the apex of the cone. In using the Jenkers device, the cap is removed by hand and placed in the hole in the cone where it is retained by gravity and is later replaced on the needle hub by pressing the needle and syringe down into the cap.

OBJECTS:

The Safety Needle Cap Handler operates by a completely different means than prior inventions and affords several advantages over prior art in this field.

The needle cap is held in the Safety Needle Cap Handler by engaging the annular ridge near the rear of the cap against a retaining shoulder by pressing the cap towards the shoulder with a retaining spring at the closed end of the needle cap, thus creating a mechanical lock instead of frictional retention. Since the needle cap is reliably held by the Safety Needle Cap Handler during all phases of the uncapping, recapping, and removal process, the danger of an infectious needle stick injury when removing or replacing the cap is eliminated.

Because, once learned, the one-handed operation afforded by the Safety Needle Cap Handler is easier and more convenient than the old two-handed removal and replacement method, compliance in its use is more likely than with the inconvenient manual safety techniques or the two-handed removal and storage, one-handed replacement of the previously existing device(s).

Risk of cross-infection to the patient is reduced when compared to the "scoop" technique since the needle and its protective needle cap do not touch the potentially contaminated counter top.

Further objects and advantages of the Safety Needle Cap Handler will become apparent from a consideration of the drawings and ensuing description thereof.

DRAWINGS:

FIG. 1 is a typical needle and needle cap showing the annular ridge.

FIG. 2 is the preferred embodiment of the Safety Needle Cap Handler with cavities for two different length needle caps and mounted in a horizontal position.

FIG. 3 is an external view of an alternate embodiment in which the retentive shoulder is cast into the body of the device instead of be provided by a separate part.

FIG. 4 is a cross section demonstrating the process of seating the needle cap into the needle cap handler.

DESCRIPTION:

The preferred embodiment of the Safety Needle Cap Handler consists of a Block (FIG. 2-3) of durable material approximately 6 centimeters by 4 centimeters in length and width and 2 centimeters in thickness, with specially shaped cavities or troughs (5) to accommodate the short and long needle caps and retaining springs. In preparing the cavities in the Block, a round bottomed trough (5) open to the near end of the Block is created for each length needle cap 1.1 centimeters wide by 1.3 centimeters deep by 3.5 centimeters and 5 centimeters long respectively. An overhang or "roof" (7) is allowed to remain over the 0.75 centimeter of the trough furthest from the open end. At this far end of the trough, a 4 millimeter hole is bored approximately 1 centimeter beyond the end of the trough to contain a retaining coil spring (6) which protects approximately 1 centimeter into the trough when seated in the hole. This spring applies pressure to the closed end of the needle cap when it is in the trough and forces it towards the open end of the trough. An internal shoulder (8) is provided at the open end of the trough reducing the trough to 0.85 centimeters wide by 1.2 centimeters deep at the open end. This may be accomplished by affixing a plate (4) with "U-shaped" notches of that size centered on the troughs or by casting the block with the shoulder integral to the block (FIG. 3). This internal shoulder at the open end of the trough will engage the annular ridge (FIG. 1-2) on the needle cap as it is driven towards the open end by the retaining spring. Screws (9) are used to secure the Block to a vertical or horizontal surface.

OPERATION:

In the preferred embodiment, the needle cap is removed from a loaded syringe by placing the tip of the needle cap at a downward angle into the trough and sliding it under the overhang and towards the closed end of the trough, compressing the retaining spring. When the needle cap has been moved far enough towards the closed end of the trough for the annular ridge on the outer surface of the cap to be beyond the internal shoulder at the open end of the trough, the back end of the syringe is brought in line with the trough bringing the rearmost, narrow portion of the needle cap into the "U-shaped" notch formed by the internal shoulder at the open end of the trough (FIG. 4). The syringe is then withdrawn in line with the trough allowing the raised annular ridge on the outer surface of the needle cap to engage the internal shoulder at the open end of the trough. The syringe is further withdrawn leaving the cap behind in the trough and held in place by the pressure of the retaining spring holding the needle cap against the internal shoulder. The closed end of the needle cap is prevented from escaping from the trough by the partial overhang or "roof" at the closed end of the trough.

The needle is recapped by inserting the tip of the needle into the open end of the needle cap and pressing the syringe forward into the cap until the cap is firmly seated on the hub of the needle and the retaining spring is compressed until the needle cap reaches the end of the trough. The rear of the syringe is then lifted until the raised annular ridge of the needle cap no longer engages the internal shoulder at the open end of the trough. The syringe is then allowed to slide back from the end of the trough and lifted from the trough.

The above description is specific to the preferred embodiment of the invention and should not be viewed as a limitation of its scope. Many variations are possible to the above design within this scope, such as elimination of the retaining springs if the device is to be mounted horizontally. The device could be molded into a dental cabinet or tray or even the back of a dental chair. As there are so many possible variations of the basic invention, the scope of the invention should be determined not by this embodiment but by the appended claim and its legal equivalents.

What is claimed is:

1. A device for removing the protective cover from a dental syringe unit, the syringe unit including a syring needle and a protective cap consisting of a generally cylindrical body adapted to removably cover said needle and thereby provide a protective cover for the needle, said cylindrical body defined by a first and second end axially disposed from one another, a rim circumferentially disposed on the cap body at a point axially disposed between the two ends of the cap, said device comprising:
   (a) a housing;
   (b) at least one opening in the housing to accomodate at least a portion of the cylindrical cap; and
   (c) means on the housing engaging at least a portion of the rim whereby the cap can be removed from the syringe unit when a force is applied axially to the syringe needle.

* * * * *